(12) United States Patent  (10) Patent No.: US 6,616,603 B1
Fontana  (45) Date of Patent: Sep. 9, 2003

(54) ANOSCOPE

(75) Inventor: Paolo Fontana, Modena (IT)

(73) Assignee: Sergio Bicocchi, Modena (IT)

( * ) Notice: Subject to any disclaimer, the term of this patent is extended or adjusted under 35 U.S.C. 154(b) by 0 days.

(21) Appl. No.: 10/084,371

(22) Filed: Feb. 28, 2002

(51) Int. Cl.$^7$ ................................ A61B 1/06
(52) U.S. Cl. ................. 600/199; 600/170; 600/179; 600/184; 600/189; 600/248
(58) Field of Search ................ 600/170, 175, 600/184, 200, 248, 245, 246, 173, 185, 190

(56) References Cited

U.S. PATENT DOCUMENTS

| | | | | |
|---|---|---|---|---|
| 357,216 A | * | 2/1887 | McCall | ............ 172/610 |
| 4,037,588 A | * | 7/1977 | Heckele | ............ 600/191 |
| 4,638,792 A | * | 1/1987 | Burgin | ............ 600/212 |
| 4,834,067 A | | 5/1989 | Block | |

FOREIGN PATENT DOCUMENTS

| | | |
|---|---|---|
| DE | 830 544 | 2/1952 |
| DE | 965 061 | 5/1957 |
| FR | 919.697 | 3/1947 |
| WO | WO 01/60238 A1 | 8/2001 |

* cited by examiner

*Primary Examiner*—John Mulcahy
(74) *Attorney, Agent, or Firm*—Birch Stewart Kolasch & Birch LLP

(57) ABSTRACT

An anoscope for surgery and/or inspection comprising:
- a tubular body (2) having a distal blind end and a proximal open end;
- an inner light reflecting surface (7) located at said distal blind end;
- at least one slot (3) formed in said tubular body;
- a light source (6) placed in light reflection relationship with said inner reflecting surface (7), and
- a maneuvering handle (5) arranged to act on said proximal end of said tubular body (2).

7 Claims, 2 Drawing Sheets

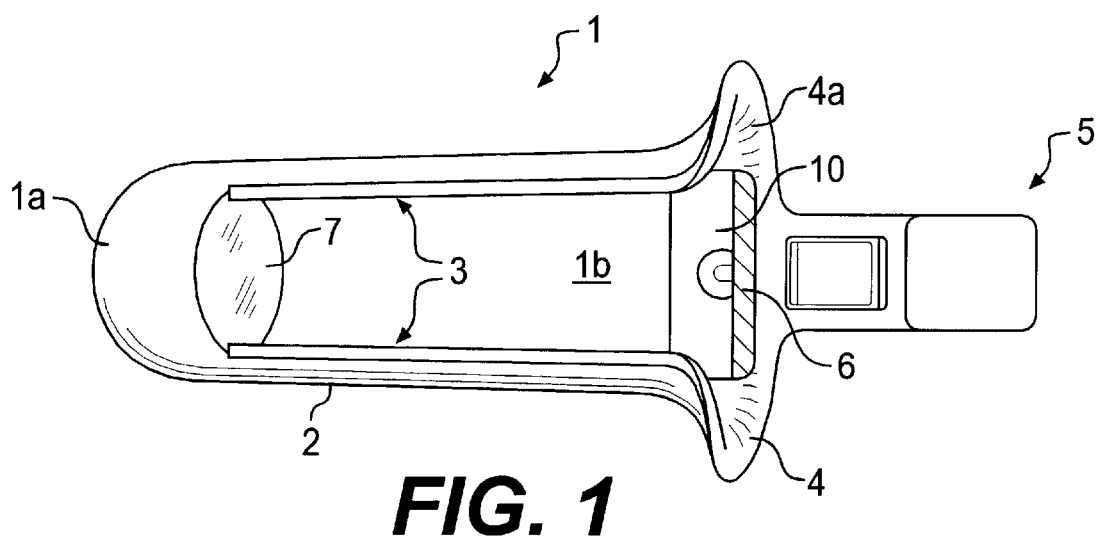
FIG. 1
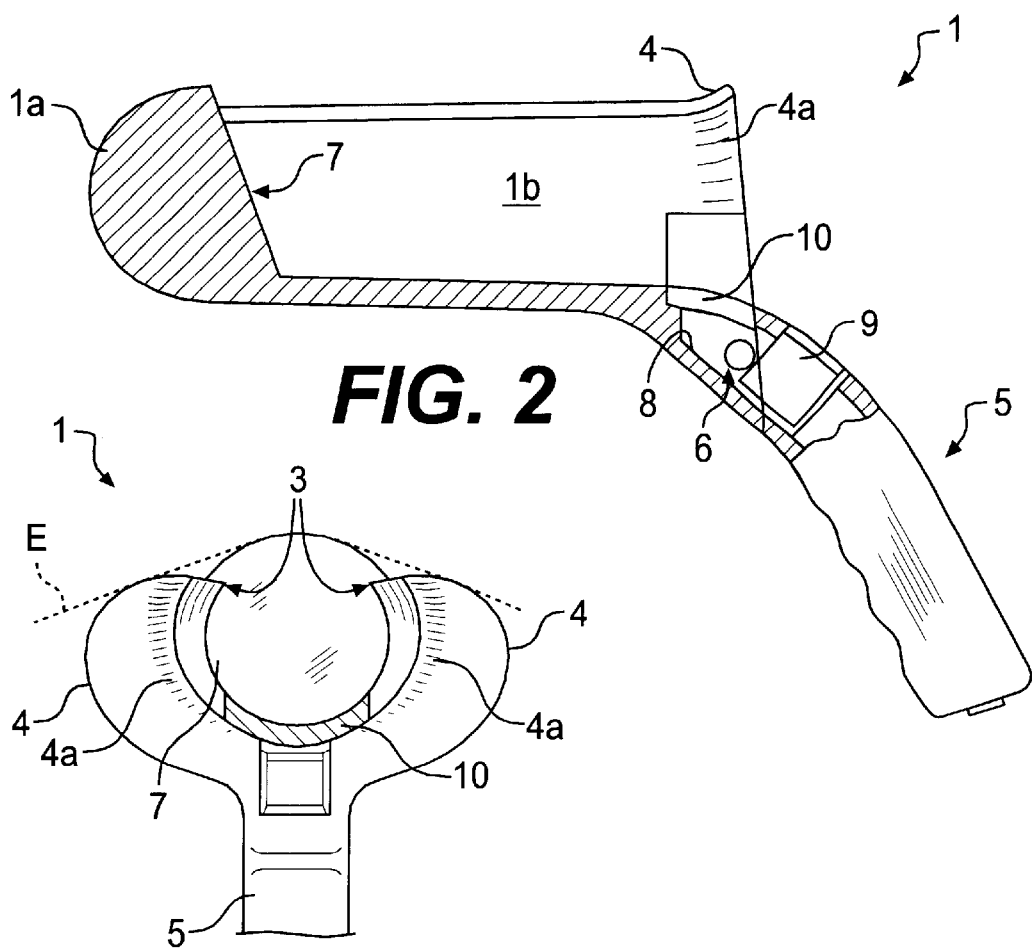
FIG. 2
FIG. 3

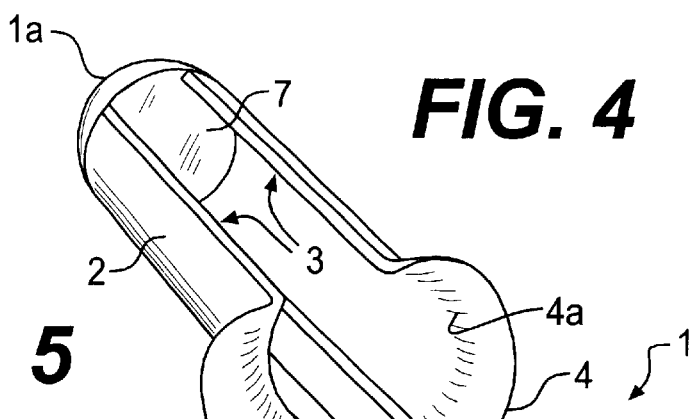
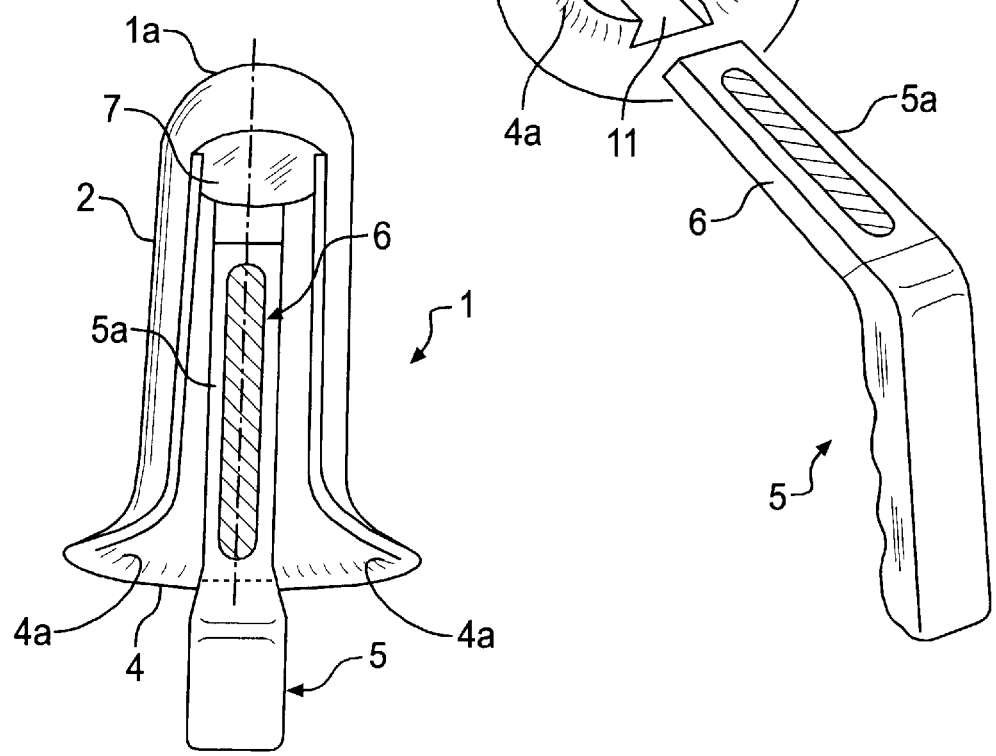
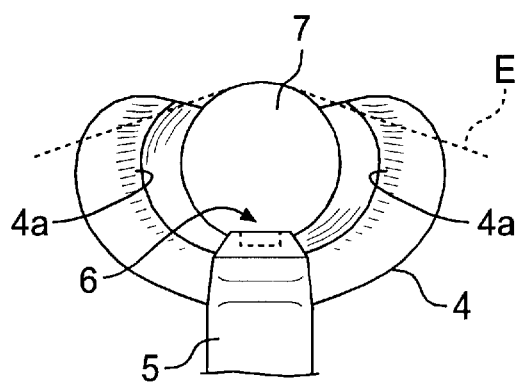

ANOSCOPE

The present invention relates to an anoscope for surgical use or to be used as a probe.

Anoscopes are instruments specifically constructed to allow medical operators to view the region of the anal orifice and the initial tract of the rectum, by dilating the anal opening. They have long been used in the medical field to examine the anorectal region.

These instruments are formed as cylindrical bodies or retractor flaps.

In the first instance, such cylindrical bodies have diameters calibrated for insertion in the anal canal and are internally provided with a cavity with an open bottom end; insertion is made possible by using appropriately provided cylindrical insertion instruments, which have a rounded end and are removed once the operation has been completed, to leave the cylindrical bodies in place in order to allow the operator to view the exposed regions, onto which light is shed by a light source (lamp or optical fiber) which is also provided. The source is integrated in a handle for manoeuvering the cylindrical body, which is arranged at the end directed toward the operator.

In so far as the present description is concerned, the end directed towards the operator is called "proximal end", and the opposite end is called "distal end".

In the second case, the flaps of the retractors (known as Eisenhammer's, Ferrand's, Park's retractors) are rounded in shape, so as to define a sort of ogive in a clustered closing configuration, in order to facilitate insertion through the anal orifice, and they are provided with means for locking the flaps in a divaricated position when they are operatively arranged inside the rectum.

No light source is provided in this type of anoscope.

In the first instance all inspection or surgery is carried out through the longitudinal opening, whereas in the second instance it is made possible through the divaricated flaps.

Both the above described types of anoscope suffer from some drawbacks which make them substantially cumbersome to use and in some cases painful and even dangerous for the patient.

For cylindrical anoscopes, the main problems are the confined viewing and operating field and the unsteady illumination of the region to be viewed that can be achieved.

In the second case, control of the retractors is an extremely delicate procedure that relies on the tactile sensitivity of the medical operator, since no means suitable for limiting their opening is provided on such retractors; if the patient has a muscle configuration which is particularly resistant to divarication, or if the operator proceeds with excessive force, the patient may in fact suffer painful traumas, which sometimes damage the integrity of the sphincter muscles, with the typical ensuing consequences associated with it.

Moreover, once the flaps of the retractors are positioned and divaricated to allow operation, they partially or even fully reduce the visual-operating field formed between the flaps.

This is due to the natural collapse that the rectal mucous membrane is subject to.

Moreover, the flaps of the retractors are usually made of durable material which can be accordingly reused on several patients, albeit every time after appropriate sterilization; if this sterilization is not performed properly, it entails the risk of promoting transmission of germs among different patients.

The object of the present invention is to solve the above described problems of the prior art, by providing a anoscope for surgery or inspection, which is sterile and disposable, that allows a precise viewing of better illuminated stretches of the field of view for inspection or surgery, with respect to what has been hitherto possible in the devices of the state of the art; that is automatic, i.e. not needing auxiliary tools, atraumatic in every respect, and allowing medical operators to carry out surgery and inspection with better comfort, in comparison with the conventional anoscopes currently used.

This aim and these and other objects which will become better apparent hereinafter are accomplished by a anoscope for surgery and inspection, comprising:

a tubular body having a distal blind end and a proximal open end;

an inner light reflecting surface located at said distal blind end;

at least one slot formed in said tubular body;

a light source placed in light reflection relationship with said inner reflecting surface; and a maneouvering handle arranged to act on said proximal end of said tubular body.

Further characteristics and advantages of the present invention will become better apparent from the description of a preferred embodiment of an anoscope for surgery and inspection, illustrated only by way of non-limitative example in the accompanying drawings, wherein:

FIG. 1 is a top view of the anoscope for surgery and inspection according to a first embodiment of the invention;

FIG. 2 is a phantom side view thereof;

FIG. 3 is a view of the proximal end of the anoscope;

FIG. 4 is perspective view of the anoscope according to a second embodiment of the invention;

FIGS. 5 and 6 are corresponding views of the anoscope, as seen from above and from the proximal end of the anoscope in the embodiment of FIG. 4.

With reference to the figures, reference numeral 1 designates an anoscope for surgery and inspection, comprising in a usual manner a cylindrical body 2 which is axially hollow and has at least one straight longitudinal opening 3 on its lateral surface; said longitudinal opening is blind on one side, namely at the distal end. At the distal end a solid tip 1a is also provided, said tip being anatomically contoured and rounded so as to facilitate insertion of the anoscope in the anal orifice, while at the proximal open end a peripheral collar 4 is provided, which is adapted to retain the perianal epidermis when the anoscope 1 is inserted, and a manoeuvering handle 5 is provided. Said handle is provided with a light source 6.

In the anoscope 1, the internal distal transverse wall 7, which is practically the bottom of an axial cavity 1b defined inside the cylindrical body 2, is suitably tilted so as to form an acute angle with the surface defined by the edges of opening 3. Said wall 7 is provided with a reflective surface in order to reflect the light beam from source 6 in cavity 1b and through said opening 3, and to reflect the image of the field of view that is being inspected.

The light source is embedded in the wall of the axial cavity 1b and at level with it, forming a single surface therewith substantially without discontinuities; in particular, in a first embodiment of the anoscope, the light source 6 is located at the proximal end of cavity 1b, in a suitable recess 8 formed at the root of manoeuvering handle 5, and is provided with a connector 6 for connection to a power source and with a transparent cover 10 whose outer surface is at level with the wall of axial cavity 1b, as already mentioned, in an essentially continuous fashion.

In a second embodiment of the anoscope 1, the light source 6 is integral with the handle 5, or more precisely it is arranged inside an elongated element 5a of the handle 5, which is angled with respect to the handle 5, integral therewith and can be inserted in a bayonet-like fashion in a corresponding seat 11 formed longitudinally in cavity 1b. The element 5a is advantageously transparent (or has a transparent portion) and has a cross-section whose profiles can be mutually slidingly mated with the profiles of said seat 11, said profiles preferably having a dovetail shape.

At the proximal end, the anoscope 1 has a peripheral collar 4, which forms a profile 4a on its outer face which is significantly flared and continuous with the wall of the axial cavity 1b and is suitable for facilitating insertion and maneoeuvering, of conventional medical-surgical operating instruments through said longitudinal opening 3, in a diagonal direction as well.

The present invention can be operated as follows: anoscope 1 for surgery and inspection is inserted in the anal orifice of the patient in a conventional manner, facilitated by the anatomically rounded contoured shape of tip 1a.

Once the anoscope is in position, the operating field is already in full exposure without the need to carry out additional adjustments; in practical terms, the tissues are properly stretched according to their normal anatomy and the rectal mucous membrane itself does not collapse, accordingly leaving the operating field provided by the anoscope completely free.

The light source 6 emits a light beam, which diffuses inside the axial cavity 1b until it is reflected by the reflective surface of the internal distal transverse wall 7, which directs the reflected beam through it toward the internal wall of the rectal region, lighting it along the entire length of said opening, by virtue of being tilted to form an acute angle with the surface defined by the edges of the longitudinal opening 3 itself.

The light source 6 can be a simple lamp or optical fibers: in both cases, in the first embodiment of the anoscope 1 the positioning can be provided in a recess 8 provided for this purpose in the region for coupling the handle 5 to the cylindrical body 1 and provided with a transparent cover 10, or, in the second embodiment, in an elongated element 5a which protrudes from the handle 5 and acts as a means for coupling it to the body of the anoscope 1, engaging with a bayonet-like coupling in a corresponding seat 11 formed longitudinally in the cavity 1b, to which it is coupled by means of interpenetrating cross-sections having a dovetail profile.

In both embodiments, the light source 6 is, as a whole, at level with the internal surface of the axial cavity 1b in order to eliminate all obstacles to viewing or to insertion of operating instruments.

The insertion and movement of the instruments for all operations are further facilitated by the significant flaring 4a of the peripheral collar 4, which is normally provided in order to retain the perianal epidermis, shown in dashed lines and designated by the letter E, at the proximal end of the anoscope 1. The flaring allows in fact to twist the instruments with respect to the longitudinal axis of the cavity 1b by an angle which is significantly greater than possible in known anoscopes.

The anoscope 1 according to the invention is produced in different and calibrated diameters and is strictly disposable and sterile.

In practical terms it has been observed that the described invention achieves the intended aim and objects.

The invention thus conceived is susceptible to numerous modifications and variations, all of which are within the scope of the inventive concept. All the details may furthermore be replaced by other technically equivalent elements.

In practice, any materials can be used; likewise any shape and dimensions can be implemented, according to requirements without thereby abandoning the scope of the protection defined in the appended claims.

What is claimed is:

1. An anoscope for surgery and/or inspection comprising:

a tubular body having a distal blind end and a proximal open end;

an inner light reflecting surface located at said distal blind end;

at least one slot formed in said tubular body;

a light source placed in light reflection relationship with said inner reflecting surface, and a maneuvering handle arranged to act on said proximal end of said tubular body wherein said maneuvering handle is engageable with and removable from said tubular body and has engaging means suitable for removably securing said handle to said tubular body; wherein the engaging means comprises a dove tail shaped coupling formed in said tubular body starting from said proximal end thereof and a tongue member form in, and extending from, said maneuvering handle;

and wherein the light source is supported by said tongue member.

2. An anoscope as claimed in claim 1, wherein said distal blind end comprises an ogival outer surface.

3. An anoscope as claimed in claim 1, wherein said proximal open end comprises a flared peripheral edge.

4. An anoscope as claimed in claim 1, wherein at least one of said slots extends longitudinally with respect to said tubular body.

5. An anoscope as claimed in claim 1, wherein the said manoeuvering handle is rigid with said tubular body.

6. An anoscope as claimed in claim 5, wherein the said light source is arranged at an intermediate location between said tubular body and said manoeuvering handle.

7. An anoscope as claimed in claim 1, wherein the said light source extends throughout a predetermined length.

* * * * *